United States Patent
McLaughlin et al.

(10) Patent No.: US 8,217,004 B2
(45) Date of Patent: Jul. 10, 2012

(54) SEQUESTERING AGENT FOR MICRONUTRIENT FERTILISERS

(75) Inventors: Mike McLaughlin, Fullerton (AU); Samuel Stacey, Aberfoyle Park (AU); Enzo Lombi, Encounter Bay (AU)

(73) Assignee: Adelaide Research and Innovation Pty. Ltd., Adelaide, South Australia ( * ) Notice: Subject to any disclaimer, the term of this patent is extended or adjusted under 35 U.S.C. 154(b) by 885 days.

(21) Appl. No.: 11/886,391

(22) PCT Filed: Mar. 15, 2006

(86) PCT No.: PCT/AU2006/000334
§ 371 (c)(1), (2), (4) Date: Jun. 13, 2008

(87) PCT Pub. No.: WO2006/096912
PCT Pub. Date: Sep. 21, 2006

(65) Prior Publication Data
US 2008/0293570 A1    Nov. 27, 2008

(30) Foreign Application Priority Data
Mar. 15, 2005   (AU) ................. 2005901235

(51) Int. Cl.
C07K 14/32 (2006.01)
A01N 43/16 (2006.01)
A01N 33/00 (2006.01)
A31K 38/04 (2006.01)
A61K 31/7028 (2006.01)

(52) U.S. Cl. .......... 514/15.5; 514/25; 504/209; 504/326

(58) Field of Classification Search .................. None
See application file for complete search history.

(56) References Cited

U.S. PATENT DOCUMENTS
3,854,923 A * 12/1974 Ott ................................ 71/1
4,786,307 A * 11/1988 Marihart ........................ 71/11
6,884,759 B2   4/2005 Hayashi

FOREIGN PATENT DOCUMENTS
WO   WO 02/059063   *   8/2002

OTHER PUBLICATIONS

Razafindralambo et al. (Journal of Surfactants and Detergents 2004, 7, 41-46).*
definition: general Oxford Dictionaries (accessed 2010).*
Mulligan et al. Environ. Sci Technol. 1999, 33, 3812-3820.*
Mulligan et al. Engineering Geology 2001, 60, 371-380.*
Gunther et al. Applied and Environmental Microbiology 2005, 71, 2288-2293.*

* cited by examiner

*Primary Examiner* — Johann Richter
*Assistant Examiner* — Jessica Kassa
(74) *Attorney, Agent, or Firm* — Renner Kenner Greive Bobak Taylor & Weber

(57) ABSTRACT

According to the present invention, there is provided a method of sequestering micronutrients when used to provide the micronutrients to a plant, which comprises applying to an area of the plant or soil/substrate surrounding the plant an effective amount of a plant fertilizer composition comprising a surfactant, such as general formula (III), that is capable of forming coordinate bonds with micronutrients.

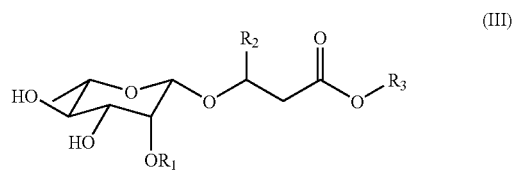

(III)

7 Claims, 2 Drawing Sheets

SEQUESTERING AGENT FOR MICRONUTRIENT FERTILISERS

FIELD OF THE INVENTION

The present invention relates to a composition and method for improving the bioavailability of micronutrients to plants.

DESCRIPTION OF THE PRIOR ART

Agriculture is a multi-million dollar industry. In order to improve plant growth good fertile soils are required and, in the absence of these, fertilisers are often used in order to facilitate the growth of agricultural crops.

Essential nutrients for plant growth include metal ions, such as Cu, Zn, Mn, etc. which are crucial to various metabolic pathways of plants such as photosynthesis and so forth. Traditional farming methods have resulted in general deficiency of such metal ions in soil and indeed in some areas these metal ions are almost completely absent and this can result in diminished yields and poor plant growth of crops grown in such areas. It is well known that the addition of surplus metal ions to either the soil or plant foliage can help to significantly alleviate such growth deficiencies in agricultural crops. One of the more common ways of delivering the appropriate metal micronutrient has been to form a chelated complex of the metal ion with a synthetic chelate as this maintains the metal ion in a soluble form for ease of application and reduces metal adsorption and fixation in soil.

However, the use of the synthetic chelates, although widely used, has some significant drawbacks such as high cost associated with production and, more recently, concerns over the fact that they are synthetic and may persist in the environment for extended periods of time. Accumulation in soil and waterways due to the recalcitrant nature of synthetic chelates may lead to some negative impact on the environment.

Examples of synthetic chelates include EDTA, EDDHA, DTPA and NTA.

Moreover, EDTA is such an efficient complexor of metal ions that it can compete with the plants for the metal ion, thus resulting in inefficiencies in delivery of the metal ion to the plant.

In addition to the use of synthetic chelates, it has also been known to use organic acids, such as citrate, as the chelating agent, however, this is found not to be generally acceptable due to inferior stability constants at pH's greater than 7 and the rapid biodegradation of citrate in the soil. Moreover, the use of acids as chelating agents also has a drawback in relation to the corrosive nature of such compounds and the damaging effect that this can have on machinery if inadvertently mixed in high concentrations.

In each of the above cases, the use of synthetic chelates or organic acids have become the standard accepted way of providing micronutrients to plants on the thought that such agents were the best possible and most efficient compounds available. Clearly, with society's changing views on agriculture and in particular a more accepted view of organic agriculture wherein synthetic agricultural compounds are not accepted due to their potential damaging effects along the food chain, there is then a need to develop more acceptable chelating agents for the delivery of micronutrients to plants.

OBJECT OF THE INVENTION

It is an object of the present invention to provide new metal chelating compounds that are capable of delivering micronutrients to plant crops.

It is a further object of the present invention to provide a method of providing micronutrients to plants that is significantly more environmentally friendly than those currently in use.

A further problem with the use of EDTA is its inability to biodegrade in the environment. EDTA can be found in many natural waterways and is often found in high concentrations in waste water effluents. Because of its lack of ability to biodegrade, EDTA has been banned in some parts of Europe and indeed other countries may soon follow suit.

A further problem with the use of NTA is that it has carcinogenic properties. Because of its toxicity and inability to biodegrade, NTA has been banned in the United States of America and indeed other countries may soon follow suit.

It is an object of the present invention to overcome, or at least substantially ameliorate, the disadvantages and shortcomings of the prior art.

Other objects and advantages of the present invention will become apparent from the following description, taking in connection with the accompanying drawings, wherein, by way of illustration and example, an embodiment of the present invention is disclosed.

SUMMARY OF THE INVENTION

The summary of the invention is as follows:

What we have found then is that by employing a compound being a surfactant having the general formula (I) and in particular a surfactant of the general formula (III), being the biosurfactant rhamnolipid, in which the single carboxylate group has the capability of sequestering micronutrient ions such as copper, zinc, manganese, iron etc. This then results in the formation of what is hereinafter referred to as a "lipid soluble" complex wherein the term "lipid soluble" refers to the ability of the chelated or complexed metal to permeate through the plant membranes or cuticle to provide the metal ion to the plant. This then is in contrast to the action of EDTA and other conventionally used chelating agents, which are not generally absorbed by plant roots and indeed are known to compete against the plant roots for the micronutrients present in the rhizosphere, being the zone that surrounds the roots of the plants. Moreover, when a rhamnolipid or other biologically produced sequestering agent are used, the biodegradation of the sequestering agent is dramatically greater than that of the synthetic chelating agents therefore resulting in less pollution and greater acceptance in the wider community. Additionally, they may also obtain organic registration, thus permitting the use of such agents in organic farms and the like. Conventional synthetic chelating agents cannot be used on organic farms due to the fact that they are synthetically manufactured.

It has also now been discovered that the use of sequestering agents produced from *Bacillus* bacteria, such as surfactin, also have the ability to sequester or complex with micronutrients such as those previously mentioned and have an increased level of biodegradability compared to that of synthetic complexing agents.

In addition, it has been discovered that these biosurfactants, having both hydrophobic and hydrophilic groups, are also able to provide transportation of the micronutrients through the foliage. The hydrophobic leaf cuticle is the main barrier for fertiliser uptake when micronutrients are applied directly to the plant foliage. We have found that rhamnolipid—metal complexes can be absorbed into hydrophobic zones thus transporting micronutrients from an aqueous phase into a lipophilic phase.

According to the present invention, although this should not be seen as limiting the invention in any way, there is provided a method of sequestering micronutrients when used to provide the micronutrients to a plant, which comprises applying to an area of the plant or soil/substrate surrounding the plant an effective amount of a plant fertiliser composition comprising a surfactant capable of forming coordinate bonds with the micronutrients, transporting the micronutrients across a membrane of the plant and releasing the micronutrients for use by the plant.

In preference, the surfactant has the general formula (I):

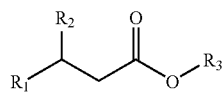

wherein $R_1$ is a hydrophilic group, and $R_2$ is a hydrophobic group and $R_3$ is selected from the group consisting of hydrophilic and hydrophobic groups.

In preference, $R_3$ is a hydrophilic group.

In preference, $R_1 = (C_3\text{-}C_6)$ cyclic alkyls or $(C_1\text{-}C_{10})$ alkyls, each of which may be interrupted by one heteroatom selected from the group consisting of O, S and N; $R_2 = H$, $(C_1\text{-}C_{10})$ saturated, mono or polyunsaturated alkyl or $(C_3\text{-}C_6)$ cyclic alkyls, and $R_3 = H$, $(C_1\text{-}C_{10})$ saturated, mono or polyunsaturated alkyls, $(C_3\text{-}C_6)$ cyclic alkyls, or Na, Ca or K.

In preference the surfactant is a biosurfactant produced from the group of bacteria consisting of *Bacillus* or *Pseudomonas* bacteria.

In preference, when the *Bacillus* group is selected the biosurfactant is surfactin.

In preference, $R_1$ has the structure (II):

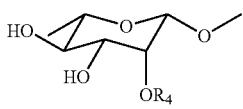

wherein $R_4 = H$, $(C_1\text{-}C_{10})$ saturated, mono or polyunsaturated alkyl or unsubstituted α-L-rhamnopyranosyl.

In preference, the molecular weight of the biosurfactant is between 450 and 700 atomic mass units.

In preference, the composition is in a form selected from the group consisting of liquids, suspensions, dispersions, emulsions, powders, and pellets.

In preference, the composition further includes a pesticide and/or insecticide.

In preference, the composition is applied to the foliage of the plant, soil or other substrate, seeds, fruits shoots, flowers or nuts.

In a further aspect of the invention there is provided a method of increasing the bioavailability of nutrients to plant roots or foliage, comprising applying an effective amount of a plant fertilizer composition comprising one or more rhamnolipids with the general formula (III)

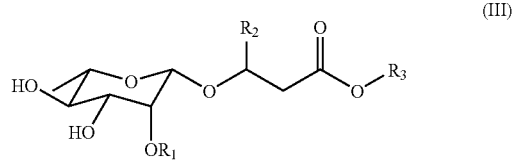

wherein $R_1 = H$, unsubstituted α-L-rhamnopyranosyl, $R_2 = H$, $(C_1\text{-}C_{10})$ saturated, mono or polyunsaturated alkyl, $R_3 = H$, $(C_1\text{-}C_{10})$ saturated, mono or polyunsaturated alkyl, —$CHR_4$—$CH_2CO_2R_6$, where $R_4 = $—$(CH_2)_x$—$CH_3$, wherein x=4-10 and $R_6 = H$, Na, Ca, K.

In preference, $R_1$ is a hydrophilic group, and $R_2$ is a hydrophobic group and $R_3$ is selected from the group consisting of hydrophilic and hydrophobic groups.

In preference, $R_3$ is a hydrophilic group.

In yet a further aspect of the invention there is described a plant fertiliser composition including a surfactant capable of forming coordinate bonds with soil micronutrients and transporting the coordinated micronutrients across a membrane of the plant and releasing the micronutrients for use by the plant, when used to increase the rate of micronutrient uptake by the plant.

In preference, the surfactant has the general formula (I):

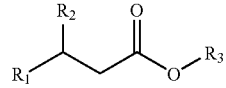

wherein $R_1$ is a hydrophilic group, $R_2$ is a hydrophobic group and $R_3$ is selected from the group consisting of hydrophilic and hydrophobic groups.

In preference, $R_3$ is a hydrophilic group.

In preference the surfactant is a biosurfactant produced from the group of bacteria consisting of *Bacillus* or *Pseudomonas* bacteria.

In preference, when the *Bacillus* group is selected the biosurfactant is surfactin.

In preference, $R_1 = (C_3\text{-}C_6)$ cyclic alkyl or $(C_1\text{-}C_{10})$ alkyl, each of which may be interrupted by one heteroatoms selected from the group consisting of O, S and N; $R_2 = H$, $(C_1\text{-}C_{10})$ saturated, mono or polyunsaturated alkyl, and $R_3 = H$, $(C_1\text{-}C_{10})$ saturated, mono or polyunsaturated alkyl, Na, Ca or K.

In preference $R_1$ has the structure (II):

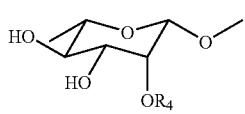

wherein $R_4 = H$, $(C_1\text{-}C_{10})$ saturated, mono or polyunsaturated alkyl or unsubstituted α-L-rhamnopyranosyl.

In preference, the molecular weight of the biosurfactant is between 450 and 700 atomic mass units.

In preference, the composition is in a form selected from the group consisting of liquids, suspensions, dispersions, emulsions, powders, and pellets.

In preference, the composition includes a pesticide and/or insecticide.

In preference, the composition is applied to the foliage of the plant, soil or other substrate, seeds, fruits shoots, flowers or nuts.

In preference, the composition is applied as a seed coat or pre-treatment to the seed prior to planting.

In preference, the composition is applied in combination with the micronutrients, either alone or in combination, Mn, Zn, Cu, Fe, Ni.

In preference, the composition is applied either alone or in combination with the macronutrients N, P, K, S, Ca, Mg.

As will be appreciated by those skilled in this particular field, the invention will have many other uses in other related industries such as horticulture and aquaculture, wherever there is a need to supply micronutrients

BRIEF DESCRIPTION OF THE DRAWINGS

By way of example, an employment of the invention is described more fully the renown for with reference to the accompanying drawings, in which.

DETAILED DESCRIPTION OF THE INVENTION

Having now generally described the invention, a further understanding can be obtained by reference to certain specific examples that are provided herein for purposes of illustration only and are not intended to be limiting.

n-Octanol/Water Partition Coefficients of Zn-Rhamnolipid Complexes n-Octanol/water partition coefficients ($K_{ow}$) are commonly used to determine whether molecules can partition into hydrophobic (lipid-soluble) phases. Polar molecules, ie metals, generally partition in the water phase. Neutral, lipid soluble organic molecules may partition within the octanol phase according to their $K_{ow}$. Most conventional chelate complexes (ie $ZnEDTA^{2-}$) partition within the water phase.

The partition coefficient has been defined as:

$$K_{ow} = \frac{C_O}{C_W}$$

where $C_o$ and $C_W$ referred to the concentration of Zn in the n-octanol and water phase respectively (Chiou et al. 1977).

The aim of this experiment was to determine whether Zn-Rhamnolipid complexes would partition within the n-octanol phase. $K_{ow}$'s were measured with varying Rhamnolipid concentrations.

Methods $K_{ow}$'s were determined using the shake-flask method. 20 ml of 1 mM $ZnSO_4.7H_2O$ solution was mixed with Rhamnolipid biosurfactant in 50 ml polyethylene tubes. Final Rhamnolipid concentrations were (mM) 0, 0.1, 0.24, 0.5, 1, 1.5, 2, 2.5. Two millilitres of n-Octanol was added to the solutions before they were shaken end-over-end for 24 hours. Following shaking, 3 ml of solution was removed from the water phase and digested in concentrated $HNO_3$ before analysis for total Zn by ICP-OES. The partition coefficient was calculated according to the equation above.

Results

Figure 1:
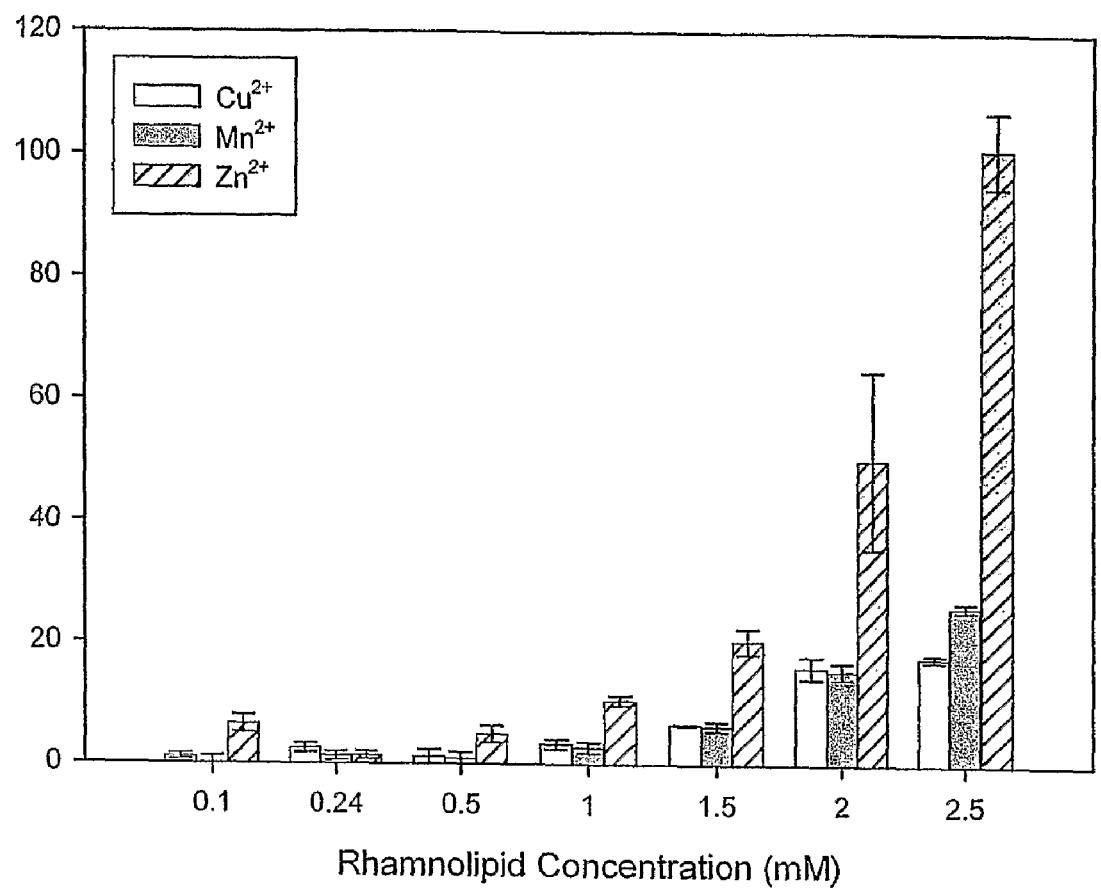
FIG. 1 is a graph of octanol-water partition coefficients of metal ion with varying rhamnolipid concentrations.

Unlike the Rhamnolipid, EDTA complexes with Zn, Mn and Cu did not partition within the n-octanol phase, as shown in FIG. 1. Clearly then the use of Rhamnolipid dramatically facilitates the transfer of the metal ion from the aqueous phase into the octanol phase.

The Use of Rhamnolipid to Sequester Zn on Alkaline and Calcareous Soils

The purpose is to determine whether Rhamnolipids would increase the availability of Zn fertiliser to Canola grown on alkaline and calcareous soils. The performance of this ligand was benchmarked against EDTA, the most commonly used chelating agent on alkaline and calcareous soils in Australia.

Materials and Methods

A pot experiment was designed to test the availability of Zn to Canola when applied to calcareous and alkaline soils either as $ZnSO_4.7H_2O$ or sequestered with, Rhamnolipids or EDTA.

Soil samples were collected from field sites known to be Zn responsive at Streaky Bay, South Australia and Birchip, Victoria (Table 1). Topsoils from each location were collected, oven dried and passed through a 2 mm sieve. The experimental fertilisers were mixed with 20g of soil, which was banded between 100 g of the unfertilised bulk soil. Total nutrient application equated to (μg/g soil) P 60, N 27, applied as TGMAP, and Zn 0.2 as $ZnSO_4.7H_2O$. Chelate rates were based on the concentrations required to complex between 75 and 100% of the Zn in the fertiliser solution. Rates varied depending on the equilibrium constant (logK) and the stoichiometry of the Zn-ligand complexes. GEOCHEM was used to predict the degree of chelation in the EDTA and Rhamnolipid fertiliser solutions. Chelate application rates were (μM/g soil) Rhamnolipid 1.25 (75% of Zn complexed), EDTA 0.37 (100% Zn complexed), Experimental controls were chelate free ($ZnSO_4$ only) and chelate and Zn free. Each treatment was replicated four times.

Two pre-germinated Canola seeds (variety *Pinnacle*) were transferred to each pot. The pots were watered to θg=0.5 with deionised water every second day and evaporation was reduced with polyethylene beads, which were spread over the exposed surface of each pot. The plants were grown for 21 days in a controlled environment growth chamber (10 h dark at 15° C., 14 h light at 20° C., 41% humidity) before the shoots were harvested, rinsed, dried, weighed and then digested in concentrated $HNO_3$. Plant digests were analysed for $^{65}Zn$ by gamma spectroscopy and for total nutrient contents by ICP-OES.

Analysis of Data

Data for shoot dry weight, shoot nutrient concentrations and Zn fertiliser uptake were analysed by analysis of variance (ANOVA). Significance between means was determined using the Least Significant Difference (LSD) test.

Results

TABLE 1

Properties of the soils used for the experiments[a].

| Site | Soil description and Classification | Carbonate (%) | pH ($H_2O$) | % Clay |
|---|---|---|---|---|
| Streaky Bay | Calcareous grey sandy loam | 39 | 8.7 ± .02 | 25 |
| Birchip | Sodosol light clay | 2.8 | 8.8 ± 0.01 | 40 |

[a]oven dry soil.

Figure 2:
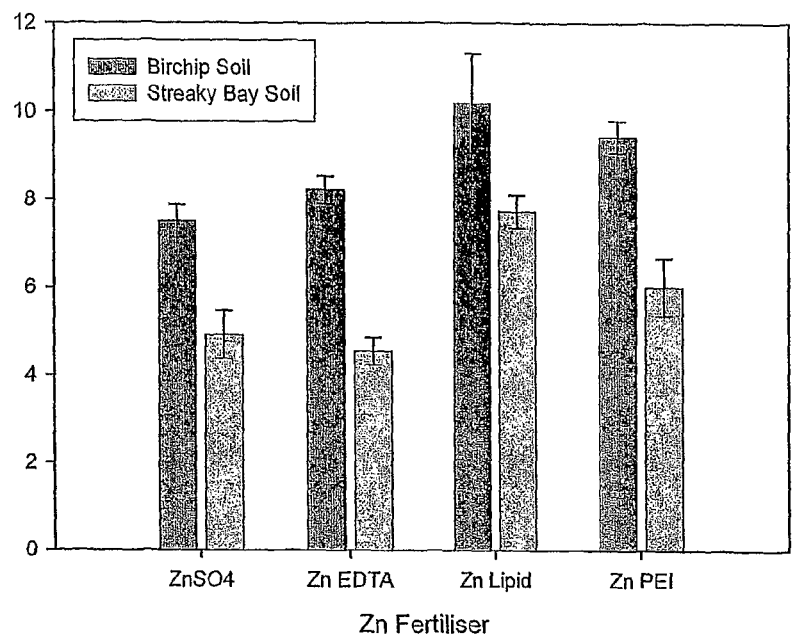
FIG. 2 is a graph of Total Zn absorbed by canola roots and translocated into shoots (±1 S.E)

EDTA was ineffective on both the calcareous grey sandy loam from streaky bay and the Sodosol from Birchip, Victoria (FIG. 2) (LSD=1.72). This result was not unexpected, as the efficacy of EDTA is known to decrease with increasing pH (Norvell 1972). Rhamnolipid significantly increased total Zn uptake by canola on both soils (p<0.01).

The published logK for ZnEDTA is 16.5 whereas the published logK for Zn-rhamnolipid is only 5.9 (Martell and Smith 1974; Ochoa-Loza et al. 2001).

Canola Dry Matter Response to Foliar Applied Zn

Foliar sprays are commonly used to apply micronutrient fertilisers to growing crops. The leaf cuticle, a hydrophobic waxy layer, represents the major barrier for nutrient absorption by leaves. Previous scientific reviews have shown that lipophilic molecules should, in theory, diffuse across cuticles more readily than charged solutes (Schonherr and Riederer 1989). However, to date, the foliar application of lipophilic fertilisers has not been widely tested. In a previous experiment Zn-Rhamnolipid complexes were found to readily partition within the hydrophobic n-octanol phase, suggesting that these complexes possess lipophilic qualities.

The aim of this experiment was to determine whether Canola shoots would absorb neutral Zn-Rhamnolipid complexes more readily than $ZnSO_4$ or ZnEDTA. Dry matter response in Zn deficient Canola was used as a measure of fertiliser effectiveness because it considers metabolically available Zn, rather than total Zn uptake.

Methods

Pre-germinated Canola seedlings (var. *Pinnacle*) were grown in Zn free nutrient solution, in a controlled environment growth chamber (10 h dark at 15° C., 14 h light at 20° C., 41% humidity) for three weeks. After 13 days, whole shoots were immersed in $ZnSO_4 \cdot 7H_2O$ solutions for five seconds. The solutions contained (_M Zn) 10, 100, 1000, and were either complexed with EDTA and Rhamnolipid, or ligand free. EDTA rates were (μM) 3.75, 37.5 or 375 and Rhamnolipid rates were (mM) 1, 1.1 or 1.9. Rhamnolipid rates were high enough to ensure a Zn $K_{ow}$ of at least 50 at the highest Zn application rate. Rhamnolipid free solutions contained 0.1% v/v Spreadwet 1000 wetting agent to enhance Zn uptake by reducing the surface tension of the solutions. Wetting agent was not required in the Rhamnolipid solutions because of the surfactant properties of the ligand.

Following shoot immersion, roots were rinsed twice in Zn-free hydroponic solutions to ensure that Zn applied to the surface of shoots did not contaminate the root systems.

After the three-week growth period, plant roots and shoots were harvested, dried and weighed for dry matter production.

Results

Figure 3:
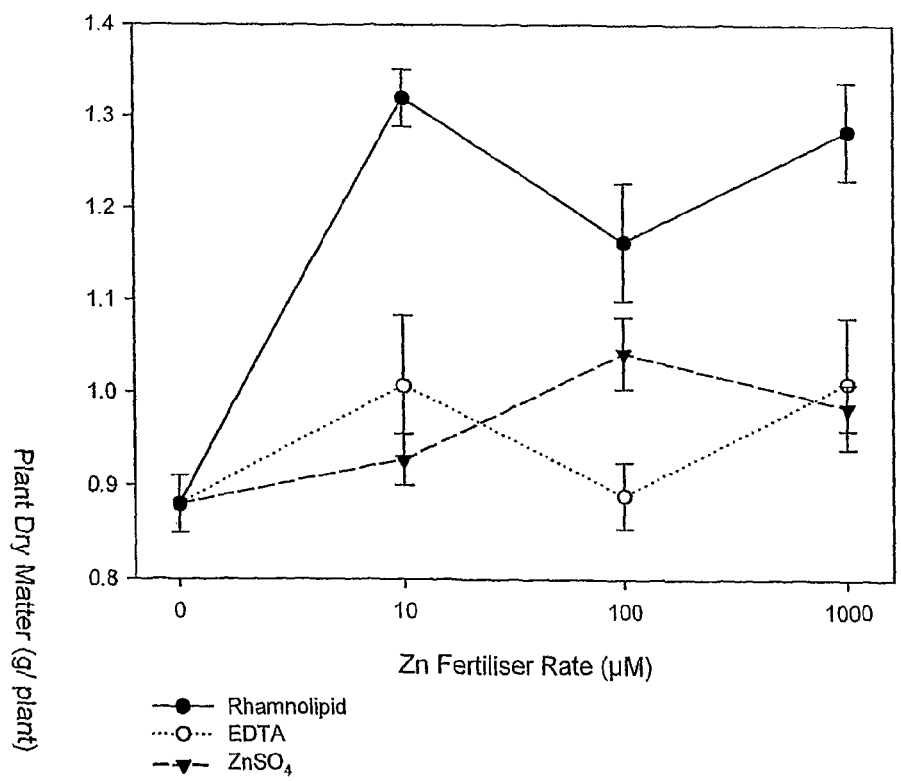
FIG. 3 is a graph of plant foliar dry matter response to applied Zn.

As shown in FIG. 3, Rhamnolipid significantly increased dry matter response to Zn (P<0.05, LSD=0.1496), which suggests that the Rhamnolipid may have increased Zn absorption through the plant foliage, compared with $ZnSO_4$ or ZnEDTA. Visual observations indicated that plants supplied with Zn-Rhamnolipid had a larger leaf area and less chlorosis than those supplied with ZnEDTA or $ZnSO_4$.

Although the invention has been hearing shown and described in one is conceived to be the most practical and preferred embodiment, it is recognized that departures can be made within the scope of the invention, which is not to be limited to the details described herein and that modifications may be made that do not depart from the scope of the invention so as to embrace any and all equivalent compositions and methods.

References

Chiou C T, Freed V H, Schmedding D W and Kohnert R L 1977 Partition coefficient and bioaccumulation of selected organic chemicals. Environ. Sci. Technol. 11, 475-478.

Martell A E and Smith R M 1974 Critical Stability Constants Volume 1: Amino Acids. Plenum Press, Inc., New York.

Norvell W A 1972 Equilibria of metal chelates in soil solution. In Micronutrients in agriculture, Eds J J Mortvedt, P M Giordano and W L Lindsay. pp 115-138. Soil Science Society of America, Inc., Madison.

Ochoa-Loza F J, Artiola J F and Maier R M 2001 Stability constants for the complexation of various metals with a rhamnolipid biosurfactant. J. Environ. Qual. 30, 479-485. Kaschl A, Romheld V and Chen Y 2002 Cadmium binding by fractions of dissolved organic matter and humic substances from municipal solid waste compost. J. Environ. Qual. 31, 1885-1892.

Schonherr J and Riederer M 1989 Foliar penetration and accumulation of organic chemicals in plant cuticles. Reviews of environmental contamination and toxicology 108, 1-70.

Stevenson F J 1994 Stability constants of metal complexes with humic substances. In Humus Chemistry: Genesis, Composition, Reactions. pp 405-428. John Wiley & Sons, Inc., New York.

The invention claimed is:

1. A method of increasing the uptake of micronutrients by a plant which comprises applying to an area of a plant, or soil/substrate surrounding the plant, an effective amount of a plant fertiliser composition comprising a surfactant capable of forming coordinate bonds with the micronutrients, the surfactant transporting the micronutrients across a membrane of the plant and releasing the micronutrients for use by the plant wherein the surfactant has the formula

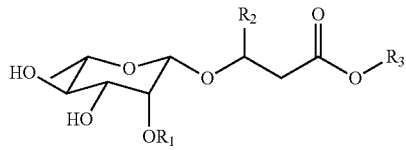

wherein $R_1$=H, ($C_1$-$C_{10}$) saturated, mono or polyunsaturated alkyls or unsubstituted α-L-rhamnopyranosyl, $R_2$=H, ($C_1$-$C_{10}$) saturated, mono or polyunsaturated alkyl or ($C_3$-$C_6$) cyclic alkyls, and $R_3$=H, ($C_1$-$C_{10}$) saturated, mono or polyunsaturated alkyls, ($C_3$-$C_6$) cyclic alkyls, or Na, Ca, Mg or K.

2. A method of increasing the uptake of micronutrients by a plant which comprises applying to an area of a plant, or soil/substrate surrounding the plant, an effective amount of a plant fertiliser composition comprising a surfactant capable of forming coordinate bonds with the micronutrients, the surfactant transporting the micronutrients across a membrane of the plant and releasing the micronutrients for use by the plant wherein the surfactant is surfactin.

3. The method of claim 1, wherein the molecular weight of the biosurfactant is between 450 and 700 atomic mass units.

4. The method of claim 3, wherein the composition is in a form selected from the group consisting of liquids, suspensions, dispersions, emulsions, powders, granules, prills, and pellets.

5. The method of claim 4, wherein the composition further includes a pesticide and/or insecticide.

6. The method of claim 5, wherein the method further includes the addition of nutrients selected from the group consisting of micronutrients and macronutrients.

7. The method of claim 6, wherein the composition is applied to foliage of the plant, soil or other substrate, irrigation water, seeds, fruit shoots, flowers or nuts.

* * * * *